United States Patent
Pleil et al.

(10) Patent No.: US 10,555,739 B2
(45) Date of Patent: Feb. 11, 2020

(54) SNAP LINK-TYPE SURGICAL CLIP

(71) Applicant: Aesculap AG, Tuttlingen (DE)

(72) Inventors: Thomas Pleil, Bad Dürrheim (DE);
Matthias Wand, Tuttlingen (DE)

(73) Assignee: Aesculap AG (DE)

( * ) Notice: Subject to any disclaimer, the term of this patent is extended or adjusted under 35 U.S.C. 154(b) by 99 days.

(21) Appl. No.: 15/518,099

(22) PCT Filed: Oct. 12, 2015

(86) PCT No.: PCT/EP2015/073561
§ 371 (c)(1),
(2) Date: Apr. 10, 2017

(87) PCT Pub. No.: WO2016/058988
PCT Pub. Date: Apr. 21, 2016

(65) Prior Publication Data
US 2017/0296195 A1    Oct. 19, 2017

(30) Foreign Application Priority Data
Oct. 15, 2014  (DE) .......... 10 2014 114 946

(51) Int. Cl.
*A61B 17/122* (2006.01)
*A61B 17/08* (2006.01)

(52) U.S. Cl.
CPC ........ *A61B 17/1227* (2013.01); *A61B 17/083* (2013.01)

(58) Field of Classification Search
CPC ......... Y10T 24/44274; Y10T 24/44376; Y10T 24/44462; Y10T 24/4447; Y10T 24/45408;
(Continued)

(56) References Cited

U.S. PATENT DOCUMENTS 4,034,653 A    7/1977  Anderson
4,337,774 A    7/1982  Perlin
(Continued)

FOREIGN PATENT DOCUMENTS

CN    102548489 A    7/2012
CN    103153213 A    6/2013
(Continued)

OTHER PUBLICATIONS

Sundt, et al., "Booster clips for giant and thick-based aneurysms", J. Neurosurg., vol. 60, 1984, pp. 751-762.
(Continued)

*Primary Examiner* — Erich G Herbermann
(74) *Attorney, Agent, or Firm* — RatnerPrestia

(57) ABSTRACT

A surgical clip includes a first clamping leg and a second clamping leg, the two clamping legs, when in use, being movable towards each other such that they squeeze a blood vessel shut and are linked to each other via a connecting piece which applies a closing force forcing the two clamping jaws towards each other, with two additional springs being provided in addition to the connecting piece which functions as the main spring and amplifying the closing force, the additional springs being arranged in parallel to the main spring and acting in opposite directions.

18 Claims, 6 Drawing Sheets

Figure 7:
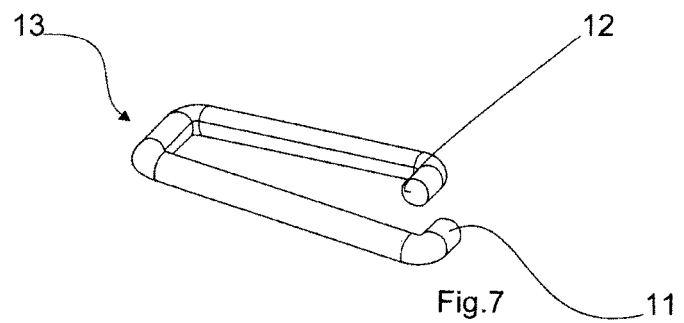

(58) Field of Classification Search
CPC .......... Y10T 24/44385; A61B 17/1227; A61B 17/083; A61B 17/128; A61B 17/1222; A61B 17/122; A61B 17/1285; A61B 2090/034
See application file for complete search history.

(56) References Cited

U.S. PATENT DOCUMENTS

| | | | |
|---|---|---|---|
| 4,932,955 | A | 6/1990 | Merz et al. |
| 4,935,026 | A | 6/1990 | McFadden et al. |
| 5,368,600 | A | 11/1994 | Failla et al. |
| 5,520,701 | A | 5/1996 | Lerch |
| 7,874,343 | B2 | 1/2011 | Hansen |
| 9,089,391 | B2 | 7/2015 | Kassab et al. |
| 9,289,216 | B2 | 3/2016 | Weisshaupt et al. |
| 2002/0111643 | A1 | 8/2002 | Herrmann et al. |
| 2004/0092961 | A1 | 5/2004 | Viola |
| 2006/0195125 | A1 | 8/2006 | Sakakine |
| 2011/0245593 | A1* | 10/2011 | Kassab .................. A61F 5/0013 600/37 |
| 2012/0184976 | A1 | 7/2012 | Nakamura |
| 2013/0184726 | A1 | 7/2013 | Weisshaupt et al. |
| 2014/0142597 | A1 | 5/2014 | Winkler et al. |
| 2014/0200598 | A1 | 7/2014 | Kassab et al. |
| 2015/0008629 | A1 | 1/2015 | Kuno et al. |
| 2016/0008001 | A1* | 1/2016 | Winkler ........... A61B 17/12031 606/157 |

FOREIGN PATENT DOCUMENTS

| | | |
|---|---|---|
| CN | 106102598 A | 11/2016 |
| DE | 8129049 U1 | 1/1982 |
| DE | 3523031 A1 | 1/1986 |
| DE | 4319829 C1 | 8/1994 |
| DE | 19723637 C1 | 11/1998 |
| DE | 19935418 A1 | 2/2001 |
| DE | 20303496 U1 | 7/2003 |
| DE | 10309491 A1 | 9/2004 |
| DE | 102006031092 B3 | 1/2008 |
| DE | 202011051881 U1 | 11/2011 |
| DE | 102010037468 A1 | 3/2012 |
| DE | 102011055094 A1 | 5/2013 |
| DE | 102012212629 A1 | 2/2014 |
| EP | 1143861 B1 | 7/2011 |
| EP | 2589346 A1 | 5/2013 |
| GB | 2161206 A | 6/1985 |
| JP | S51110146 A | 9/1976 |
| JP | 6124807 A | 2/1986 |
| JP | 2006519674 A | 8/2006 |
| JP | 2006305230 A | 11/2006 |
| JP | 2011015716 A | 1/2011 |
| JP | 2013502303 A | 1/2013 |
| RU | 2218882 C1 | 12/2003 |
| WO | 2004080275 A2 | 9/2004 |
| WO | 2013111416 A1 | 8/2013 |
| WO | 2014012718 A1 | 1/2014 |

OTHER PUBLICATIONS

"Motives Definitions, Requirements, Testing", DiN 8287, Apr. 1983, pp. 1-5, with English language translation.
German Office Action for German Application No. 10 2013 107 876.1, dated Jul. 8, 2015, including English translation—14 pages.
International Search Report for International Application No. PCT/EP2014/064610, dated Oct. 13, 2014—2 pages.
Kunne et al., "Machine Parts 1" 10th Edition, Bibliographic Information of the German National Library, ISBN pp. 1-4, with English language translation 978-3-83-51-0093-0, pp. 1-4, with English language translation.
Written Opinion of the International Search Authority for PCT/EP2014/064610, dated Oct. 13, 2014—5 Pages.
German Search Report for German Application No. 10 2014 114 946.7, dated Jul. 29, 2015, with English language translation—12 Pages.
International Search Report and Written Opinion for International Application No. PCT/EP2015/073561, dated Dec. 14, 2015—7 Pages.
Chinese Office Action for Chinese Application No. 2014/80041783.6, dated Jul. 21, 2016—12 Pages.
Japanese Office Action for Japanese Application No. 2016-517380, dated Jun. 28, 2016—4 Pages.
Japanese Office action for Japanese Application No. 2016/517380, dated Nov. 29, 2016—4 Pages.
First Chinese Office Action for Chinese Application No. 201580055996.9, dated Feb. 26, 2019, 9 pages.
Notification of Reasons for Rejection for Japanese Application No. 2017-520523, dated Jul. 16, 2019, with translation, 12 pages.

* cited by examiner

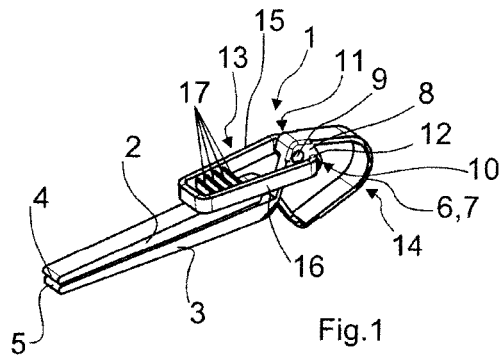
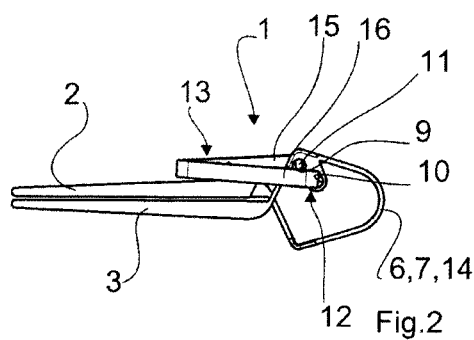
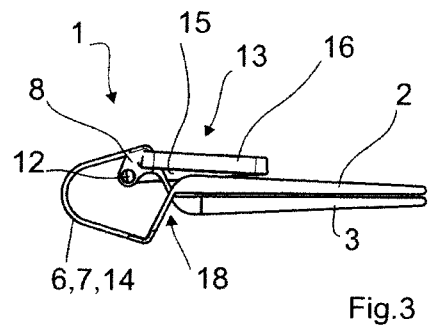
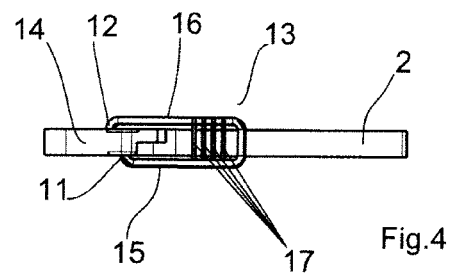
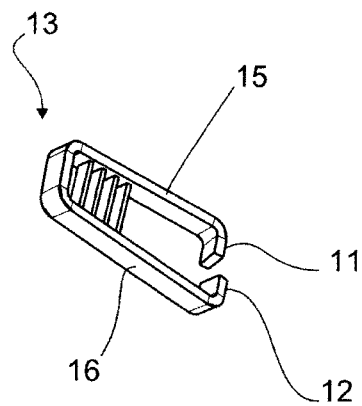
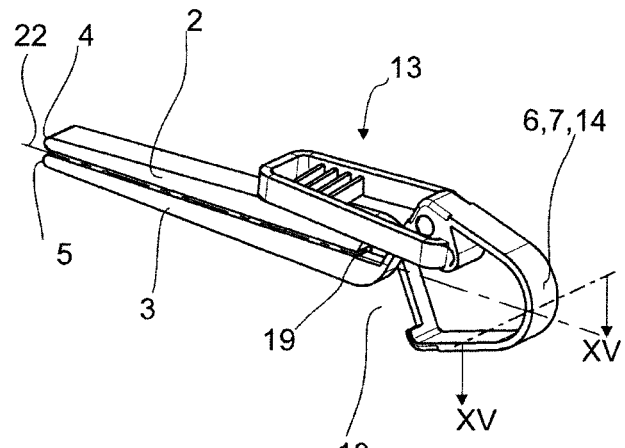

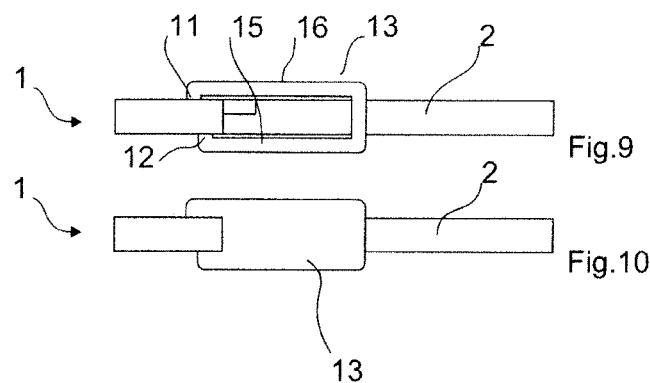
Fig.9
Fig.10
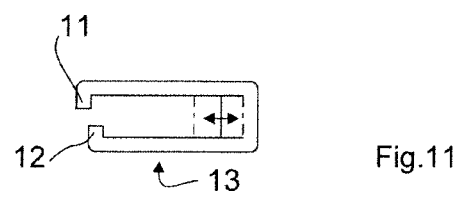
Fig.11
Fig.12
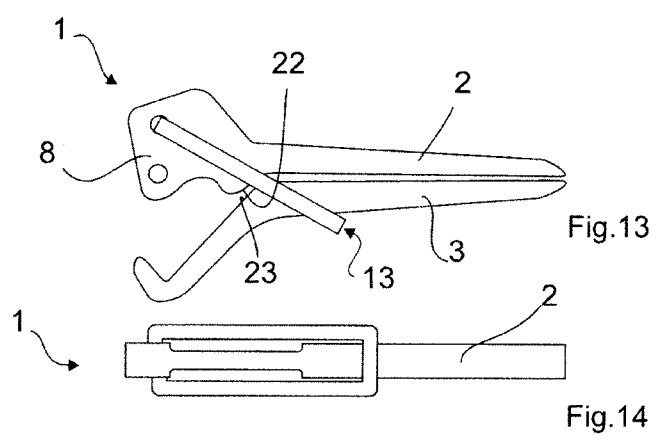
Fig.13
Fig.14

SNAP LINK-TYPE SURGICAL CLIP

RELATED APPLICATION(S)

This application is the United States National Phase of International Application No. PCT/EP2015/073561, filed Oct. 12, 2015, which is related to and claims the benefit of priority of German Application No. DE 10 2014 114 946.7, filed Oct. 15, 2014. The contents of International Application No. PCT/EP2015/073561 and German Application No. DE 10 2014 114 946.7 are incorporated by reference herein in their entireties.

FIELD

The invention relates to a surgical clip, for example in the form of an aneurysm clamp or aneurysm clip, and especially to a surgical (vessel) clip having a first clamping leg and a second clamping leg which, when in use, are movable toward each other such that they squeeze a blood vessel shut and preferably abut on each other at least in portions, for example in alignment and/or free from any projection, and are linked to each other via a connecting piece (spring element) which applies a closing force forcing the two clamping legs/clamping jaws towards each other.

BACKGROUND

From prior art, clips are known which are used for treating aneurysms. An aneurysm is understood to be a vasodilatation, especially an arterial dilatation which is colloquially also referred to as "arterial sacculation". An aneurysm is a spindle-shaped or saccular localized permanent expansion of the cross-section of blood vessels due to congenital or acquired wall modifications.

Surgical clips are used to squeeze the blood vessel, for example the arterial dilatation, shut. In so doing, two clamping legs clamp the walls of the blood vessel onto each other and prevent flow through the blood vessel.

There are existing already numerous surgical clips which are used for this purpose, for example those known from U.S. Pat. No. 4,935,026 A or U.S. Pat. No. 5,368,600 A. In the latter case a spring element of the type of a bending beam (pre-bent in U-shape or circular segment shape) is inserted in the clip. Also the use of half windings inside the clip is known, as taught in DE 43 19 829 C1, for example. There is disclosed a clamp having two legs which include bulges on their outer surfaces. The legs are resilient relative to each other and are interconnected at their foot-side ends. A clamping ring is slipped over the bulge and then forces the two legs towards each other. The clamping ring may include a pin which is used for stabilizing the connection.

A surgical clip consisting of three parts is also known from DE 199 35 418 C2. Accordingly, a surgical clip comprising two clamping arms being pivotal relative to each other about a pivot axis and in a clamping position having a clamping area substantially adjacent each other is disclosed, wherein each of the clamping arms includes a free end and an end provided with a bearing, in both bearings a joint shaft defining the pivot axis being supported, and comprising a tensioning element being associated with the two clamping arms and maintaining the latter biased in the clamping position, wherein the shaft is formed by the tensioning element.

An aneurysm clamp is known from DE 197 23 637 C1, too. There an aneurysm clamp comprising two arms each having a jaw member and an operating leg which are crossing each other is shown, wherein the operating legs are facing each other and are interconnected by a resetting means biasing the jaw members towards each other and the resetting means has a formed flat metal element describing a constant flat curve between the operating legs, the curve at least in portions taking a wave shape or a rectangular shape.

Another aneurysm clip is known from DE 81 29 049 U1. That aneurysm clip includes two legs, the one leg including a recess corresponding to the width of the other leg in a crossing area, wherein a guide bridges said recess and on both sides of the recess is connected to the one leg by spot welding. Said aneurysm clip finally makes use of a 1.5-fold winding.

A surgical clip also known as "ligature clip" is also known from DE 10 2006 031 092 B3. In order to facilitate, in the case of a surgical clip comprising two arms being interconnected by a spring element and each supporting a clamping jaw, the arms including at their outer surface an opening extending transversely to the longitudinal direction of the arms for receiving a projection of a handling instrument, the application of the handling instrument to the clip, it is suggested that the opening is surrounded by a trough-shaped guiding surface which falls from outside toward the opening.

A surgical clip including two clip legs adapted to squeeze a blood vessel shut is known from DE 10 2010 037 468 A1. In detail, a surgical clip is described there comprising two clip legs the free first ends of which fully abut on each other in the closed state of the clip, i.e. in the idle position thereof. The idle position is reached in the state of use, with merely the walls of a blood vessel still being arranged between the clip legs. The two clip legs are formed to cross each other and are connected to each other by their second ends being opposed to the free first ends via a spring element. The spring element is an integral part of the two clip legs and includes one and a half windings.

In the known surgical clips frequently the problem arises that they have to be manufactured by hand, thus preventing efficient use of machines during fabrication. Also fissuring problems, especially caused by the winding of leg springs or the bending of specific clip geometries, are known. When leg springs have been wound so far, undesired over-winding has been possible so far, thus increasing the chance of failures. It has further been difficult so far to exactly adjust the closing force. Adjusting a closing force has not been easy so far. So far, spring overload has not been excluded.

Apart from the drawbacks of insufficient closing force, common surgical clips also have a construction size which is so wide that the view to the aneurysm to be treated is obstructed when the clip is applied. For the aneurysm clamp of DE 197 23 637 C1 only a maximum closing force of 1.76 Newton is known, which corresponds to an equivalent of 180 grams.

SUMMARY

It is the object of the present invention to eliminate the known drawbacks and to provide a vessel clip which generates sufficient closing force despite a large opening width without exceeding the mechanical limits of the clip material, however.

According to the invention, this object is achieved in a generic surgical clip by the fact that in addition to the pretensioning/biasing spring acting as main spring at least one further (as well as separate) additional spring increasing/backing the closing force thereof is used/provided. In this way, an increase in bias is achieved without the already existing biasing spring having to be modified as to design or material. Thus, it is possible to provide the additional spring quasi adaptively at the vessel clip and therefore to retrofit the additional spring to already existing clip designs without any major modification measures. In addition, a securing function is realized in that the (anyway existing) additional spring need not be tensioned up to its maximum loading capacity to reach a required biasing force, but may remain below its maximum loading limit. The shortage for reaching the required biasing force then may be compensated by the additional spring.

In other words, two corresponding or interacting springs are used, wherein the two springs in active connection provide the required closing force without the individual spring being overloaded.

Preferably two additional springs are provided. When the two additional springs are arranged, e.g. symmetrically with respect to the central plane between the two clamping legs, such that they act in opposite directions and, resp., from different directions onto the clamping legs, both clamping legs are equally stressed instead of being loaded unilaterally, which might entail torsions and bending of the clip.

Advantageous embodiments shall be explained in detail in the following.

It is of advantage when the additional spring is arranged/used in parallel to the main spring, for example in the way of a so called "stereo spring".

In order to provide the additional closing force at low cost it is further advantageous when the additional spring is in the form of a yoke spring, bending beam or beam-like spring, of a torsion spring or a leaf spring. Even combinations of said individual springs are possible. If a leaf spring is used, it may be curved or bent, for example in the way of a "clicker".

In order to achieve an embodiment adapted to the case of use it is of advantage when the biasing spring (main spring) which preferably simultaneously serves as connecting piece of the two clip legs is in the form of a bending beam or a flexible spring leaf, wherein advantageously its cross-sectional geometry and/or its cross-sectional design might be defined/modified/adjusted specifically for obtaining a desired spring characteristic.

It may also be useful when the biasing spring has a cross-section varying as to its longitudinal extension, for example, or a constant rectangular, polygonal, elliptical, circular segment-shaped and/or blade-like cross-section. A blade-like cross-section may be characterized by a concave surface on the one side and a convex surface on the other side.

When the additional spring includes a force adjusting zone or force adjusting mechanism for (pre-)adjusting the additional closing force to be applied by the additional spring and backing the closing force, an operating surgeon may use clips adapted to the case of application.

It is also easy to adapt the surgical clip to the case of application on the spot, when the force adjusting zone is pre-perforated or includes predetermined breaking points for removing additional spring material preferably without the use of any tools.

This can be achieved, according to a preferred aspect of the present invention, by the fact that the additional spring is a preferably U-shaped yoke spring comprising two longitudinal legs the free ends of which are mounted on either of the two clip legs or on the connecting piece coupling the clip legs (in a hinge-like manner), wherein the longitudinal legs are interconnected via a number of cross-webs/bars spaced in the longitudinal direction of the longitudinal legs, the cross-webs being individually detachable preferably at predetermined breaking points or perforations. Of preference, the cross-web being closest to the free ends of the longitudinal legs is adjacent to the other one of the two clip legs so as to resiliently press the same against the one of the clip legs. In this way, the distance and thus the lever length between the bearing point to the other one of the two clip legs and the articulation point of the spring yoke can be varied at the one clip leg/connecting piece and in this way the effective biasing force can be adjusted.

It is further advantageous for the additional spring to include two mounting journals at the free ends of their two longitudinal legs via which mounting journals the additional spring is/will be mounted to the one clip leg/connecting piece. Accordingly, the two longitudinal legs may have different lengths relative to each other, thus causing the two mounting journals to be differently spaced from the respective closest cross-web. In this way, upon its swiveling about the asymmetric mounting journals the yoke experiences (internal) elastic deformation from which the additional biasing force is resulting.

Finally, the mounting journal may be provided to be mounted in a rotatable or rotationally fixed manner to the one clip leg or the connecting piece.

In other words, it is advantageous when the force adjusting zone/mechanism includes at least one web/bar, preferably two, three, four or more webs/bars preferably equally spaced apart from each other which connect(s) two longitudinal legs of the (yoke-shaped) additional spring which are spaced apart from each other and may be aligned in parallel to one or both clamping legs. Then one web after the other may be removed by an assistant or by the operating surgeon her-/himself so that the additional closing force is adjustable as desired so as to obtain the required clamping force, for example onto the blood vessel, after adding the closing force which is applied by the main spring.

When the additional spring is mounted on the connecting piece, for example by force closure, form closure and/or adhesive closure, preferably with press-fit, the assembly of both springs is facilitated as then only the main spring has to be mounted to the clip legs and the additional spring is thus automatically aligned with the clip legs.

Assembly becomes especially easy when the additional spring includes the two mounting journals at its two legs/free leg ends which are aligned preferably transversely, especially preferred also trigonally relative to the longitudinal axis of the additional spring and/or either of its legs, and/or point in the opposite direction, for example to the respective other leg.

When the mounting journals are offset against each other in the longitudinal direction of the additional spring or of the clamping legs, a twisting/curving of the yoke-shaped additional spring may be predetermined when it swivels about the mounting journal, the twisting/curving generating a force which is adapted to be introduced to either of the two clamping legs.

It is of further advantage when the mounting journals are provided at a first end of the additional spring and the legs of the additional spring integrally forming the mounting journals are integrally connected at a second end by the force adjusting zone. It is also useful when the web or webs is/are provided more closely to the second end of the additional spring than to the first end thereof.

The costs for the clip may be reduced when the yoke-shaped additional spring in a top view has a preferably constant rectangular, semi-circular or elliptical shape.

When a yoke spring/torsion spring is used as additional spring, the spring characteristic of the yoke spring can be defined both by the position of the two spring ends/mounting journals and by the shape/contour itself.

In one embodiment, the yoke spring has shorter webs which serve for finely adjusting the spring characteristic. This is done by detaching individual webs.

According to an additional or independent aspect of the invention, the surgical clip comprises two clamping legs which are not directly connected or are loose and which are held together and are biased relative to each other via a spring element, especially a yoke spring, being fastened to the one clamping leg and encompassing the other clamping leg. Said clip shape especially excels by its simple structure and simple mountability.

Under the afore-described aspect, the two clamping legs may have rolling surfaces at which the clamping legs are rolling during opening and closing of the clamping legs. Said surfaces adopt the function of a joint.

According to one embodiment, the rolling surfaces may be configured, especially cam-shaped, so that the course of the clamping force varies over the opening angle of the clamping legs. In particular, the rolling surfaces may be configured such that the clamping force or at least the gradient of the clamping force decreases while the opening angle increases.

Customized requirements may still be taken into account by the different arrangement of the yoke spring, on the one hand, and of the main spring, for example in the form of the flexible/bending beam, on the other hand. The solution that, unlike the state of the art, the closing force of the clip exhibits no "mono spring" but a "stereo spring" (comprising at least two separate springs arranged in parallel) offers a plurality of advantages:

A harmonized spring load is enabled by the "stereo spring".

The closing force of the clip is produced in the same plane in which it is acting.

No connection that would act around the longitudinal axis of the clip has to be accepted.

The clip itself has a very narrow design, which entails minimized material damage by mostly machine manufacture.

BRIEF DESCRIPTION OF THE DRAWING FIGURES

Figure 8:
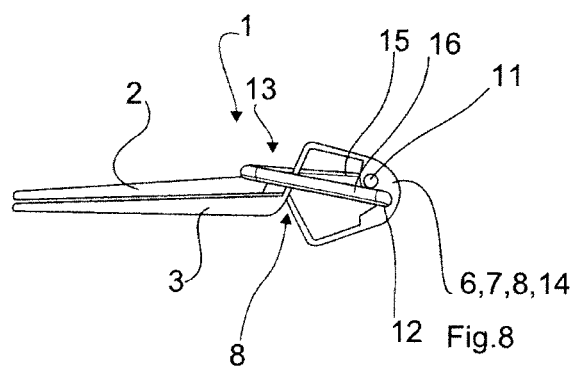
Figure 15:
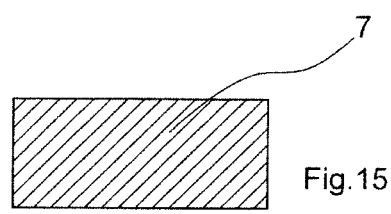
Figure 16:
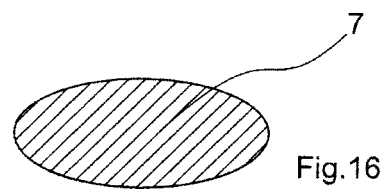
Figure 17:
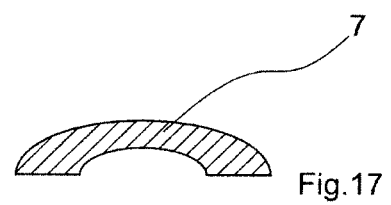
Figure 18:
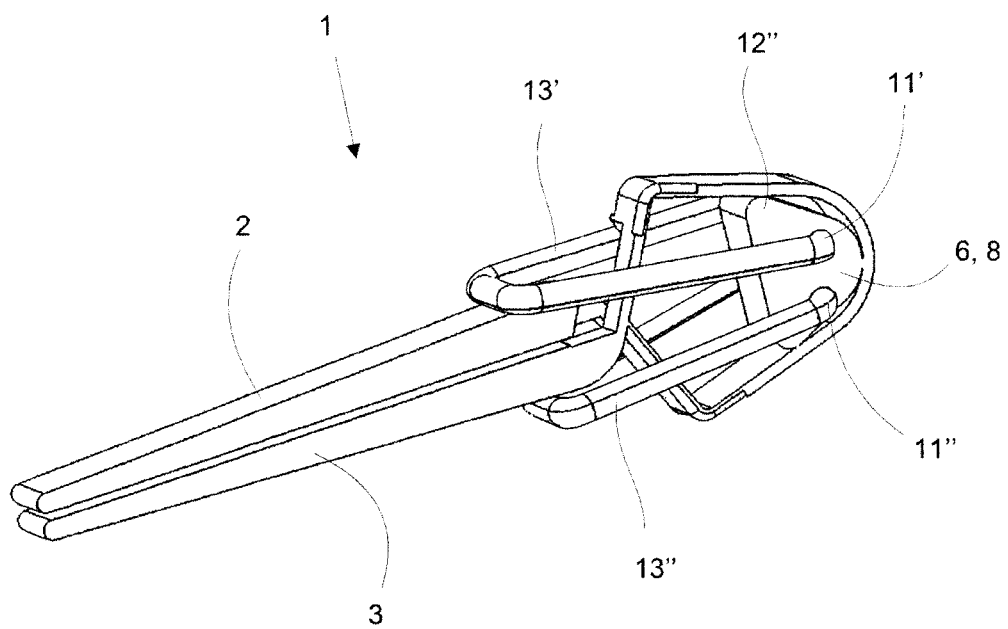

Hereinafter the invention shall be illustrated in detail by way of different embodiments with reference to the accompanying Figures, wherein:

FIG. 1 shows a perspective view of a first embodiment of a surgical clip according to the invention, FIGS. 2 and 3 show two different side views of the clip of FIG. 1, FIG. 4 is a top view of the clip of FIGS. 1 to 3, FIG. 5 is a perspective view of the additional spring used in the clip of FIGS. 1 to 4 only, FIG. 6 is another perspective view of the clip of FIGS. 1 to 5, FIG. 7 is a variant of an additional spring of the embodiment of an additional spring as shown in FIG. 5, FIG. 8 shows a further embodiment according to the invention of a surgical clip in a side view, FIG. 9 shows another variant of a clip according to the invention making use of the additional spring of FIG. 7, FIG. 10 shows the clip of FIG. 9 in a comparable view from above (top view) but including a leaf spring type additional spring, FIG. 11 is a detailed view of the leaf spring acting as additional spring of the embodiment of FIG. 10, FIG. 12 is a variant of an additional spring, FIG. 13 is another embodiment of a surgical clip according to the invention in a view from the side (side view), FIG. 14 shows the clip of FIG. 13 in a view from above (top view), FIG. 15 is a cross-sectional configuration along the line XV from FIG. 6 in the area of a connecting piece which connects the two clamping legs of the surgical clip in a resilient/biasing manner, FIG. 16 is a variant of the cross-sectional geometry of the form shown in FIG. 15, FIG. 17 is another cross-sectional geometry of the connecting piece; and FIG. 18 shows another embodiment according to the invention of a surgical clip according to the invention in a perspective view.

Figure 19:
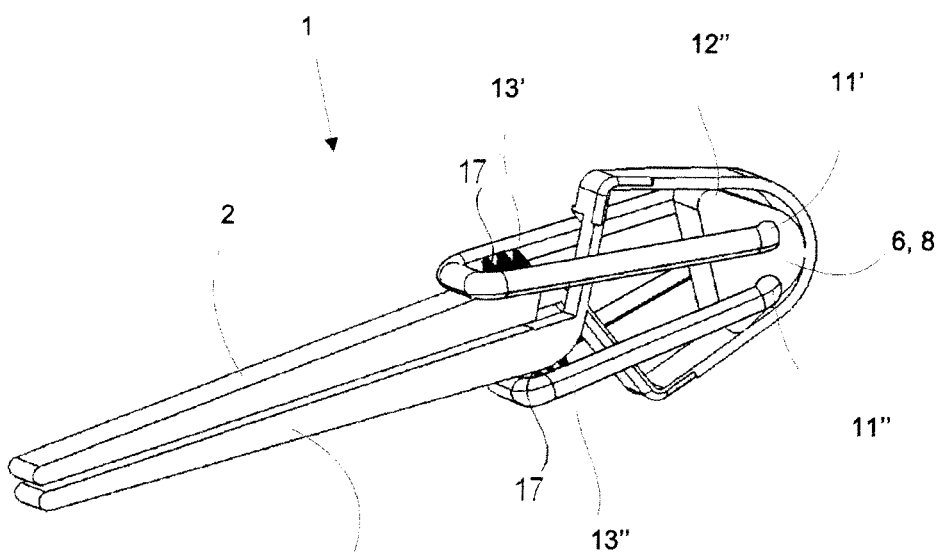

FIG. 19 shows another embodiment according to the invention of a surgical clip according to the invention in a perspective view.

DETAILED DESCRIPTION

The Figures are merely schematic and only serve for the comprehension of the invention. Like elements in each embodiment are provided with like reference numerals. Individual elements of the embodiments may be replaced with each other.

In FIG. 1 a first embodiment of a clip 1 according to the invention is illustrated. It is provided for use as an aneurysm clip. It includes a first clamping leg 2 which may also be referred to as clip leg or clamping jaw. In the idle condition (initial position of the clip) it is adjacent to or almost adjacent to a second opposite clamping leg 3. Said clamping leg 3, too, may be referred to as clip leg or clamping jaw. Each of the two clamping legs 2 and 3 includes at a distal longitudinal portion (tissue clamping) surfaces or edges facing each other which may abut, for example, on a blood vessel so as to squeeze the same shut, when in use. The two clamping legs 2 and 3 have free proximal ends 4 and 5. At the proximal free ends 4 and 5 the two clamping legs 2 and 3 are transformed into a preferably U-shaped or C-shaped connecting piece 6 which couples the clip legs in a hinge-like manner. It is noted in this context that the connecting piece includes crossing portions so that flexible compression of the U-shape or C-shape causes the two clip legs 2, 3 to be spaced apart (clip opening). It is also imaginable, however, to design the connecting piece without any crossing portions (in the way of forceps), wherein in that case the U-shape or C-shape would have to be elastically pulled apart so as to space the two clip legs 2, 3 apart from each other (clip opening).

The connecting piece 6 exhibits spring characteristics according to this embodiment. The two clamping legs 2 and 3 as well as the connecting piece 6 are formed integrally and preferably of the same material or are welded or soldered from different material elements. Preferably they are merging in a seamless manner. The connecting piece 6 consequently acts as an integral flexible beam 7 of the clip for coupling the two clip legs 2, 3 in a flexible hinge-like manner.

Furthermore, the connecting piece 6 includes in a longitudinal portion close to the second clip leg 3 an eyelet-type connecting area 8 which is provided by material thickening or material accumulation. In the connecting area 8 two (blind) holes 9 and 10 are provided which open on sides (vertical sides relative to the clamping surfaces) of the connecting piece 6 facing away from each other. It is pointed out in this context that the connecting area 8 need not necessarily be arranged on the connecting piece 6 but may alternatively be arranged on the proximal end of the second (or first) clip leg 3.

A surgical clip as described before belongs, with the exception of the connecting area, to the generally known state of the art as published in a plurality of documents. In this case, the clamping force of the clip is produced by the connecting piece 6 which simultaneously forms a (main) biasing spring. It is basically also possible, however, to couple the two clip legs in a hinge-type manner (via a pivot pin) and to mount the (main) biasing spring separately herefrom on the two clip legs. In this case, the (main) biasing spring exclusively has the function of producing a clamping force, whereas the pivotal coupling of the clip legs is effectuated separately herefrom by the pivot pin. This design, too, belongs per se to prior art and is known to those skilled in the art.

It is common to all of said designs, however, that the clamping force of the clip is generated by the (main) biasing spring.

In accordance with the invention, at least one further additional spring 13 arranged in parallel to the (main) biasing spring is provided for producing an additional clamping force which adds to the main clamping force due to the parallel arrangement. Said additional spring 13 is designed (according to the following description) such that it can be mounted on the connecting area 8.

For this purpose, the additional spring 13 is in the form of a yoke or frame comprising two longitudinal legs 15, 16 arranged substantially in parallel which at their distal ends are integrally connected by a cross leg. The yoke frame may preferably be plastically bent from a spring wire.

The longitudinal legs 15, 16 include, at the free proximal ends thereof, mounting journals 11 and 12 which are adapted to engage in the holes 9, 10 of the connecting area 8. The mounting journals 11 and 12 of the additional spring 13 are especially clearly visible in the FIGS. 5, 7, 9, 11 and 12. Accordingly, also the mounting journals 11, 12 are formed by bending the spring wire into stub-like wire extensions directed against each other, wherein the mounting journals may as well be provided in any other way such as welding or soldering, as a matter of course. Moreover, it is evident especially from FIG. 5 that the spring wire is not round in the present case but is polygonal, preferably quadrangular and the holes 9, 10 accordingly also have a quadrangular cross-section so that the (polygonal) mounting journals 11, 12 have to be inserted at a predetermined angular position relative to the clamping legs 2, 3 into the same in a rotationally fixed manner. Said angular position is selected so that the spring yoke 13 already in the initial position presses against the outer surface (side facing away from the clamping surface) of either of the clamping legs 2 and biases the same in addition to the (main) biasing spring 14 against the other clamping leg 3. While the connecting piece 6 thus acts as main spring 14, a backing force is applied to the clamping leg 2 by the additional spring 13. The closing force produced by the main spring 14 is thus supplemented and backed by an additional closing force.

As already explained in the foregoing, the additional force 13 substantially includes the two legs 15 and 16 at the proximal end of which facing the connecting area 8 the mounting journals 11 and 12 are formed. In the embodiment shown here the mounting journals have an angled cross-section, but they may as well have, as shown in FIG. 7, a cylindrical structure and thus a circular cross-section. At the end or middle portion of the additional spring 13 and, resp., of the longitudinal legs 15, 16 facing away from the connecting portion 8 a number of, presently preferably four, (cross) webs/bars 17 is provided at a longitudinal leg distance from each other, which webs additionally interconnect the longitudinal legs 15, 16 but are detachable from the additional spring 13 preferably without using any tools or by simple means. For this purpose, between the webs 17 and the two legs 15 and 16 a perforation or predetermined breaking point may be provided, which is only illustrated here in outlines. Also, a single perforation in the middle or close to the middle of the webs 17 is possible.

FIG. 2 illustrates the engagement of the angled mounting journals 11 and 12 in the holes 9 and 10 in the mounting area 8 of the connecting piece 6. As is also evident from FIG. 3, the transitions of the clamping legs 2 and 3 to the connecting piece 6 are directly juxtaposed in a crossing area 18. In FIG. 4 the webs 17 distributed equidistantly from each other between the two legs 15 and 16 of the additional spring 13 are clearly visible. The additional spring 13 shown in FIG. 5 is inserted in the holes 9, 10 in the enlarged embodiment shown in FIG. 6.

The mounting journals 11 and 12 are located at different heights. In other words, the two holes 9, 10 are not axially aligned with each other but are arranged to be offset at least transversely against the clamping legs 2, 3 (in the height direction of the clip). When, accordingly, the spring yoke is mounted in the holes 9, 10, the two longitudinal legs 15, 16 experience bending in opposite directions so that finally they are aligned to be warped.

In addition or alternatively to the afore-mentioned height distance of the two holes 9, 10, it is provided in the present case to design the longitudinal legs 15, 16 of the spring yoke 13 to have different lengths and furthermore to offset the two holes 9, 10 in the longitudinal direction of the clip corresponding to the lengthwise difference of the legs 15, 16. Both measures serve for causing elastic deformation (warping) of the spring yoke 13, when the spring yoke 13 is pivoted about the mounting journals 11, 12 thereof, due to the asymmetry of the yoke articulation, which results in a spring resetting force in the initial position of the spring yoke (according to FIG. 2).

Finally, on the surfaces of the clamping legs 2 and 3 facing each other a proximal step 19 is visible from which a specifically prepared surface structure such as corrugation extends in the direction of the distal end 4 and, resp., 5 of the clamping legs 2, 3.

The function of the additional spring 13 can be paraphrased as follows.

After mounting in the holes 9, 10 the described spring yoke 13 enters into pressing contact with a leg side facing away from the clamping surface of the one clamping leg 2 and biases the same against the other clamping leg 3. The clamping force in this case results from the offset of the two holes 9, 10 and the angular position at which the mounting journals 11, 12 have to be inserted in the holes 9, 10. If detachable webs 17 are arranged, for design reasons the spring yoke 13 with the web 17 which is closest to the holes 9, 10 and resp. the mounting journals 11, 12 abuts on the clamping leg 2. By detaching the respective closest web 17 the effective lever length of the spring yoke 13 may thus be varied and consequently the additional clamping force may be varied.

The variant of an additional spring 13 shown in FIG. 7 is formed of a round spring wire including no detachable webs 17. Such additional spring 13 including no webs 17 is adapted to be arranged, alternatively to the position of the connecting area 8 according to the afore-described embodiment, on a central portion 20 of the U-shaped or C-shaped bent connecting piece 6, as is shown in FIG. 8. When the curved shape of the connecting piece 6 is curved in the proximal direction, the central portion 20 thus has the maximum lengthwise distance from the clamping legs 2, 3 so that the yoke spring 13 is operatively engaged in the one clamping leg 2 only in a proximal end portion of the clamping legs 2, 3. Since in said central portion 20 the connecting piece 6 must have a material thickening for forming the connecting area 8, at the same time the maximally obtainable spring force of the connecting piece 6 acting as main biasing spring is increased.

Other than illustrated in FIG. 9, instead of a yoke-shaped additional spring 13 offering advantages for a regular load distribution, also a (full-surface) leaf spring may be used as additional spring, as it is shown in FIG. 10. The leaf spring 13 itself may be fully curved or bent once or several times along its longitudinal direction, for example configured in roof shape or L-shape or C-shape.

It is exactly with such leaf spring type additional springs that a fine adjustment of the spring force is possible by material removal, for example by the use of pre-perforations 21 as is shown in FIG. 12. Such additional spring 13 which then is freed from material in the area distant from the mounting journal may be used as a securing spring/torsion spring as is shown in FIGS. 13 and 14. Aneurysm clips of this type may also be used as so called "Müller clips". They may then be used in a way similar to so called "alligator clamps" or "crocodile clips".

In the clip shown in FIGS. 13 and 14 the clamping legs 2, 3 are held together merely via the yoke spring 13, with the yoke spring 13 fastened to the one clamping leg 2 encompassing the other clamping leg 3. The two clamping legs 2, 3 at their proximal ends include rolling surfaces 23, 24 facing each other which the clamping legs 2, 3 roll off when the free ends 4, 5 of the clamping legs 2, 3 are opened. At least one of the rolling surfaces 23 is formed on a cam-shaped portion of the one clamping leg 2. Due to the cam-shaped rolling surface(s) 23 the pivot point of the two legs 2, 3 varies upon opening and, resp., closing of the legs. During opening, the pivot point moves somewhat away from the free ends 4, 5 and, resp., from the contact point of the yoke spring 13 with the clamping leg 3 and, during closing, it moves somewhat toward the free ends 4, 5 and, resp., toward the contact point of the yoke spring 13. By reason of the displacement of the pivot point, the clamping force of the yoke spring 13 varies over the opening angle of the two clamping legs 2, 3. More exactly speaking, the absolute value or at least the gradient of the clamping force decreases with an increasing opening angle. The course of the clamping force can be adjusted via the cam shape and, resp., the shape of the rolling surfaces 23, 24.

The clamping legs 2, 3 are also guided somewhat laterally relative to each other via the yoke spring 13. However, for preventing the clamping legs 2, 3 which are basically held together loosely via the yoke spring 13 from laterally slipping down during opening or closing and rolling off the rolling surfaces 23, 24, the rolling surfaces 23, 24 may be appropriately designed, e.g. may include tongue and groove which cause lateral form closure between the two rolling surfaces 23, 24 of the clamping legs 2, 3.

A substantial advantage of the clip 1 shown in FIGS. 13 and 14 is the course of the clamping force variable via the opening angle while the components exhibit a very simple structure and are easy to mount.

Finally, FIGS. 15 to 17 illustrate different cross-sectional geometries for the connecting piece acting as a flexible bending beam 7 for precisely adjusting the spring characteristic of the main spring 14. Referring to FIG. 6, a longitudinal direction 22 is shown there. The sections of the FIGS. 15 and 17 are orthogonal to said longitudinal direction 22.

FIG. 18 illustrates another embodiment which substantially differs from the embodiment shown in FIG. 8 in that two identically configured additional springs 13' and 13" are provided, a first additional spring 13' of which acts on the first clamping leg 2 and, resp., is resiliently biased against the latter and a second additional spring 13" of which acts on the second clamping leg 3 and, resp., is resiliently biased against the same. The two additional springs 13' and 13" are arranged symmetrically to a central plane of the clip 1 and, resp., of the two clamping legs 2 and 3 and are also symmetrically linked to the center piece 6. Similar to the embodiment illustrated in FIG. 8, the legs of each yoke spring 13' and 13" are of different length and the mounting journals 11' and 12' and, resp., 11" and 12" are fastened to a center piece 6 being offset against each other. Alternatively, the additional springs 13' and 13" can be linked, similar to the embodiment according to FIGS. 1 to 6, to two connecting areas 8 provided on separate sides facing each other. For the rest, the description of the previous embodiments shall be referred to.

The embodiment according to FIG. 18 thus excels by the fact that two additional springs 13' and 13", more exactly speaking yoke springs, provided additionally to the main spring 14 and being arranged in parallel are provided. They act on both clamping legs 2, 3 from opposite sides/directions. By virtue of the use of two spring elements, especially by the symmetric arrangement thereof, a balanced equilibrium of forces and more uniform loading of the two clamping legs 2, 3 will be brought about than in the case of one spring element 13 acting on one clamping leg 2 only.

As a matter of course, other pairs of additional springs arranged in parallel which apply opposed spring forces or moments to the clamping legs 2, 3 may equally be applied.

FIG. 19 illustrates another embodiment like the embodiment in FIG. 18, except that the first additional spring 13' and the second additional spring 13" each have webs/bars 17 like the embodiment in FIG. 1.

The invention claimed is:

1. A surgical clip comprising: two clamping legs which are pretensioned to each other in a clip-closing-direction via a closing force of a pretensioning spring or of an elastic connecting portion such that distal free ends of the two clamping legs contact one another in a resting position of the surgical clip; two additional springs amplifying the closing force of the pretensioning spring or of the elastic connecting portion and being arranged in parallel thereto and connected to the surgical clip, the two additional springs being formed as independent and separate parts from the pretensioning spring or the elastic connecting portion and acting on the two clamping legs from opposite directions such that a first additional spring of the two additional springs exerts a force in only a first direction and a second additional spring of the two additional springs exerts a force in only a second direction, wherein the first direction is opposite the second direction, wherein the first additional spring is formed as a first U-shaped yoke spring and the second additional spring is formed as a second U-shaped yoke spring, each of the first and second U-shaped yoke springs comprising two longitudinal legs and a cross leg interconnecting the two longitudinal legs, free ends of the two longitudinal legs being mounted either on the two clamping legs or on a connecting piece coupling the two clamping legs.

2. The surgical clip according to claim 1, wherein the elastic connecting portion serves for pivotal coupling of the two clamping legs and is a bending beam.

3. The surgical clip according to claim 2, wherein the elastic connecting portion includes, in a side view thereof, a rectangular, polygon-type, elliptical or partially circular longitudinal extension.

4. The surgical clip according to claim 1, wherein the two additional springs each include a force adjusting mechanism so as to adjust an additional closing force to be applied by the two additional springs and backing the closing force of the pretensioning spring.

5. The surgical clip according to claim 4, wherein the force adjusting mechanism forms a pre-perforated portion or predetermined breaking points at the two additional springs for removing additional spring material.

6. The surgical clip according to claim 5, wherein the two clamping legs comprise a first clamping leg and a second clamping leg, and, wherein for each of the first and second U-shaped yoke springs, the two longitudinal legs are coupled via a number of cross webs spaced in a longitudinal direction of the two longitudinal legs which are individually detachable at the pre-perforated portion or predetermined breaking points.

7. The surgical clip according to claim 6, wherein the cross web closest to each of the free ends of the two longitudinal legs of the second U-shaped yoke spring abuts on the second clamping leg so as to resiliently press said cross web against the first clamping leg.

8. The surgical clip according to claim 6, wherein the two additional springs include two mounting journals at the free ends of the two longitudinal legs.

9. The surgical clip according to claim 8, wherein for each of the first and second U-shaped yoke springs, the two longitudinal legs are different in length relative to each other, thus causing the two mounting journals to be distanced differently from the respective closest cross web.

10. The surgical clip according to claim 8, wherein the mounting journals are mounted to be rotatable or to be rotationally fixed on the first clamping leg or the elastic connecting portion.

11. The surgical clip according to claim 1, wherein the first additional spring acts only on a first clamping leg of the two clamping legs and is resiliently biased against the first clamping leg, and the second additional spring acts only on a second clamping leg of the two clamping legs and is resiliently biased against the second clamping leg.

12. The surgical clip according to claim 1, wherein the two additional springs are arranged symmetrically to a central plane of the surgical clip.

13. The surgical clip according to claim 1, wherein the first additional spring is configured to contact an outer surface of a first clamping leg of the two clamping legs and the second additional spring is configured to contact an outer surface of a second clamping leg of the two clamping legs.

14. The surgical clip according to claim 13, wherein the cross leg of the first U-shaped yoke spring is configured to contact and press on the outer surface of the first clamping leg and the cross leg of the second U-shaped yoke spring is configured to contact and press on the outer surface of the second clamping leg.

15. The surgical clip according to claim 14, wherein the cross leg of the first U-shaped yoke spring is configured to contact and press on an outermost surface of the first clamping leg, and the cross leg of the second U-shaped yoke spring is configured to contact and press on an outermost surface of the second clamping leg.

16. The surgical clip according to claim 1, wherein the first additional spring acts only on a first clamping leg of the two clamping legs and is resiliently biased against the first clamping leg, and the second additional spring acts only on a second clamping leg of the two clamping legs and is resiliently biased against the second clamping leg, and the first additional spring is configured to contact an outer surface of the first clamping leg, and the second additional spring is configured to contact an outer surface of the second clamping leg.

17. A surgical clip comprising:

two clamping legs which are pretensioned to each other in a clip-closing-direction via a closing force of a pretensioning spring or of an elastic connecting portion such that distal free ends of the two clamping legs contact one another in a resting position of the surgical clip;

two additional springs amplifying the closing force of the pretensioning spring or of the elastic connecting portion and being arranged in parallel thereto and connected to the surgical clip, the two additional springs being formed as independent and separate parts from the pretensioning spring or the elastic connecting portion and acting on the two clamping legs from opposite directions such that a first additional spring of the two additional springs exerts a force in only a first direction and a second additional spring of the two additional springs exerts a force in only a second direction, wherein the first direction is opposite the second direction, wherein the two additional springs each include a force adjusting mechanism so as to adjust an additional closing force to be applied by the two additional springs and backing the closing force of the pretensioning spring.

18. The surgical clip according to claim 17, wherein the two additional springs are yoke springs, bending beams, torsion springs or leaf springs.

* * * * *